(12) United States Patent
Jallon (10) Patent No.: US 9,235,807 B2
(45) Date of Patent: Jan. 12, 2016

(54) SENSOR DETECTION DEVICE, CORRESPONDING DETECTION METHOD AND COMPUTER PROGRAM

(75) Inventor: Pierre Jallon, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 255 days.

(21) Appl. No.: 13/884,814

(22) PCT Filed: Nov. 8, 2011

(86) PCT No.: PCT/FR2011/052605
§ 371 (c)(1),
(2), (4) Date: May 10, 2013

(87) PCT Pub. No.: WO2012/062997
PCT Pub. Date: May 18, 2012

(65) Prior Publication Data
US 2013/0238543 A1    Sep. 12, 2013

(30) Foreign Application Priority Data
Nov. 10, 2010   (FR) ...................................... 10 59294

(51) Int. Cl.
| G06F 17/00 | (2006.01) |
| G06N 5/02 | (2006.01) |
| G06F 19/00 | (2011.01) |
| G06N 5/04 | (2006.01) |
| G06N 99/00 | (2010.01) |
| G06N 5/00 | (2006.01) |

(52) U.S. Cl.
CPC ................ *G06N 5/02* (2013.01); *G06F 19/345* (2013.01); *G06N 5/003* (2013.01); *G06N 5/04* (2013.01); *G06N 99/005* (2013.01)

(58) Field of Classification Search
None
See application file for complete search history.

(56) References Cited

U.S. PATENT DOCUMENTS

2012/0054133 A1    3/2012   Jallon

FOREIGN PATENT DOCUMENTS

DE    10 2007 063 008    6/2009

OTHER PUBLICATIONS

Layered representations for learning and inferring office activity from multiple sensory channels Nuria Olivera,*, Ashutosh Gargb, Eric Horvitza Received Mar. 20, 2002; accepted Feb. 2, 2004 Available online Aug. 6, 2004.*

(Continued)

*Primary Examiner* — Kakali Chaki
*Assistant Examiner* — Ababacar Seck
(74) *Attorney, Agent, or Firm* — Oblon, McClelland, Maier & Neustadt, L.L.P.

(57) ABSTRACT

A device detecting at least one scenario from predetermined scenarios wherein a physical system observed by at least one sensor is likely to be found, including: at least one sensor providing a physical system observation data sequence; a storage storing at least one statistical model associating possible observation data values with the predetermined scenarios; a computer programmed to select at least one of the scenarios based on the observation data sequence and at least one statistical model. The storage includes plural statistical models broken down into plural ordered levels between an input level, wherein each statistical model associates possible values of at least a portion of the observation data with intermediate states for the statistical model, and an output level, wherein each statistical model associating possible values of at least a portion of the intermediate states of a lower level with at least a portion of the predetermined scenarios.

11 Claims, 4 Drawing Sheets

(56) References Cited

OTHER PUBLICATIONS

Oliver N., et al., "Layered Representations for Learning and Inferring Office Activity from Multiple Sensory Channels", Computer Vision and Image Understanding, Academic Press, , vol. 96 No. 2, pp. 163-180, XP 004583829, (Nov. 1, 2004).

Jallon, P. "A Bayesian Approach for Epileptic Seizures Detection with 3D Accelerometers Sensors", $32^{nd}$ Annual International Conference of the IEEE EMBS, pp. 6325-6328, XP 031794974, (Aug. 31-Sep. 4, 2010).

Jallon, P. et al., "Detection System of Motor Epileptic Seizures Through Motion Analysis with 3D Accelerometers" 31 St Annual International Conference of the IEEE EMBS , pp. 2466-2469, XP 031639459, (Sep. 3, 2009).

International Search Report issued Jan. 1, 19,2012 in PCT/FR11/052605 filed Nov. 8, 2011.

* cited by examiner

SENSOR DETECTION DEVICE, CORRESPONDING DETECTION METHOD AND COMPUTER PROGRAM

The present invention relates to a device for detecting at least one scenario from a set of predetermined scenarios wherein a physical system observed by at least one sensor is likely to be found, on the basis of physical system observation data provided by the sensor. It also relates to a corresponding method and computer program.

The term "physical system" denotes any system producing a physical output suitable for being observed by a sensor, the system being assumed in principle to be capable of being found in a predetermined number of scenarios modelled by the detection device.

The physical system observed may for example be an inanimate object, such as a structure wherein the condition is to be monitored to detect any anomalies or deformations using one or a plurality of sensors.

It may also consist of an animate system, such as a person or an animal, for example suffering from a chronic disease having detectable episode scenarios using a sensor. According to the sensor(s) used, the detectable scenarios are variable and the applications multiple.

The invention more specifically applies to a detection device comprising:
- at least one sensor for providing a physical system observation data sequence,
- means for storing at least one statistical model associating possible observation data values with the predetermined scenarios, and
- a computer, connected to the sensor and the storage means, programmed to select at least one of the scenarios, from the plurality of predetermined scenarios, based on the observation data sequence and said at least one statistical model.

In particular, one promising application is the subject of the article by P. Jallon et al, entitled "Detection system of motor epileptic seizures through motion analysis with 3d accelerometers", published at the IEEE EMBC 2009 conference. In this article, a device for detecting epileptic seizures using motion sensors, particularly 3D accelerometers, is based on hidden Markov models, each optimally modelling, for a given scenario, the statistical properties of observation sequences provided by the sensors as expected for that scenario. In concrete terms, each hidden Markov model of this device corresponds to a predetermined possible scenario of a person subject to epileptic seizures including, for example: a first seizure scenario, a second seizure scenario different from the first, a non-seizure scenario. In this case, the detection principle consists of selecting any of the possible scenarios, by comparing probabilities of these scenarios, based on an observation sequence provided by at least one accelerometer, the probabilities being calculated on the basis of each of the hidden Markov statistical models of the device.

The example mentioned above belongs to a first application category of hidden Markov models to the detection of scenarios, wherein each scenario is modelled by a Markov model wherein the parameters are predefined to reflect the scenario optimally. According to this first application category, it is possible to determine the most suitable scenario for an observation data sequence acquired by selecting the Markov model corresponding best thereto.

According to a further application category of hidden Markov models to the detection of scenarios, as for example mentioned in the article by L. Rabiner, entitled "A tutorial on Hidden Markov Models and selected applications in speech recognition", Proceedings of the IEEE, vol. 77, no. 2, pp. 257-286, February 1989, a single statistical model is used, wherein each hidden state corresponds to one of the scenarios of the set of predetermined scenarios. The parameters of the statistical model are then defined based on prior knowledge of probabilities of each scenario/state independently of any observation, probabilities of transitions from one scenario/state to another and observation probability laws for each scenario/state. According to this second application category, it is possible to determine a sequence of scenarios/states, wherein each scenario is selected from the set of predetermined scenarios, this sequence being the most likely in view of an acquired observation data sequence. The sequence of scenarios/states based on the observation data sequence may for example be determined using the Viterbi algorithm.

Therefore, it is noted that both application categories mentioned above are associated with solving different types of problems. However, the examples mentioned above have, in common, the property of directly linking the overall observation with the decision associated with the scenarios (selection of a scenario or determination of a sequence of scenarios/states) using the predefined statistical model(s).

In this way, if the observation is multi-valued, i.e. if, at each time, a plurality of observation parameters are provided using one or a plurality of sensors, known detection devices are particularly sensitive to at least partial or temporary failures of one of the parameter sources, whether the source is a sensor or a specific chain for processing signals from a sensor. Indeed, such failures affect the decision directly.

Moreover, known detection devices are inflexible in that they are not readily suitable for adding or removing a sensor or a specific chain for processing signals from a sensor.

In this way, it may be sought to provide a detection device suitable for eliminating at least some of the problems and constraints mentioned above.

Therefore, the invention relates to a detection device such as that mentioned above, wherein the storage means comprise a plurality of statistical models broken down into a plurality of ordered levels between:
- a first level, or input level, wherein each statistical model associates possible values of at least a portion of the observation data with specific intermediate states for the statistical model, and
- a final level, or output level, wherein each statistical model associates possible values of at least a portion of the intermediate states of a lower level with at least a portion of the predetermined scenarios.

In this way, the observation data is merely indirectly associated with the possible scenarios, by means of internal states of the device specific to the predefined statistical models and stored in memory according to at least two ordered levels. The input level particularly makes it possible, with the intermediate states, to act as a buffer between the observations and the decision relating to the scenarios, to remedy the failures mentioned above.

Furthermore, the flexibility of the resulting detection device is enhanced due to the fact that the addition of a sensor or a particular processing chain may affect only one input level statistical model directly, without disturbing the determination carried out by the computer based on the output level model(s).

Advantageously, the computer is programmed for:
- determining a sequence of standardised measurement values of at least a portion of the intermediate states based on at least one statistical model defined to determine that portion of the intermediate states and on values received by the statistical model, and selecting said at least one scenario, on the basis of the sequence of standardised measurement values and at least one output level statistical model.

The term "standardised measurement values" denotes, for a given statistical model, that the sum at each time of the intermediate state measurement values thereof, wherein each is preferably positive, is equal to a time-independent constant. In other words, a measurement value of an intermediate state suitable for being determined by a given statistical model is referred to as "standardised" if the sum of the measurement values of all the intermediate states suitable for being determinable by this statistical model and at the same time is equal to a selected time-independent constant.

Standardising the intermediate state value determination used for observations for at least one output level statistical model further offers the advantage of at least partially preventing some observation parameters provided by the sensor from concealing others, for example merely in that they take values in different scale ranges.

Optionally, the computer is programmed to determine a sequence of standardised measurement values of all the intermediate states based on all the statistical models defined to determine the intermediate states and on values received by the statistical models.

In principle, it is thus possible to adjust the relative importance to be assigned to each statistical model defined to determine intermediate states. In particular, it is possible to assign the same constant for all the sums of measurement values associated with all the statistical models concerned. This offers the advantage of equating all the observation parameters.

Also optionally, the standardised measurement values are probability values. This represents the specific scenario wherein all the measurement values are positive and standardised to the value 1.

Also optionally, at least one statistical model of a level other than the output level is a hidden Markov model and the computer is programmed to determine a sequence of probability values of at least a portion of the hidden states thereof iteratively on the basis of a data sequence provided at the input of the Markov model according to a recurrence relation between successive values of the probability value sequence, this recurrence relation involving a single value, dependent on the recurrence index, of the input data sequence provided.

Also optionally, the recurrence relation takes the following form:

Initialisation:

$$\tilde{p}(X_0 = i | Y_0) = p(X_0 = i) p(Y_0 | X_0 = i) \text{ and}$$

$$p(X_0 = i | Y_0) = \frac{\tilde{p}(X_0 = i | Y_0)}{\sum_j \tilde{p}(X_0 = j | Y_0)},$$

Recurrence on N:

$$\tilde{p}(X_{N+1} = i | Y_{0:N+1}) =$$

$$\sum_j p(X_N = j | Y_{0:N}) p(Y_{N+1} | X_{N+1} = i) p(X_{N+1} = i | X_N = j) \text{ and}$$

$$p(X_{N+1} = i | Y_{0:N+1}) = \frac{\tilde{p}(X_{N+1} = i | Y_{0:N+1})}{\sum_j \tilde{p}(X_{N+1} = j | Y_{0:N+1})},$$

where i represents the hidden state index in question, N the sequence index, Y the statistical process representing the input data sequence provided, and X the statistical process corresponding to the most suitable hidden state sequence for the input data sequence.

Also optionally:
the output level comprises a Markov statistical model wherein the hidden states correspond to the predetermined scenarios and wherein the observations are chosen from estimated intermediate state values provided by the computer, and
the computer is programmed to output a sequence of scenarios, wherein each is selected from the predetermined scenarios, on the basis of the sequence of intermediate state values and the output level Markov statistical model.

Also optionally:
the output level comprises a hidden Markov statistical model for each scenario from the set of predetermined scenarios, wherein the observations are chosen from estimated intermediate state values provided by the computer, and
the computer is programmed to select an output level Markov model on the basis of the sequence of intermediate state values and to output the corresponding scenario.

Also optionally, at least one statistical model of a different level to the input level and the output level is a hidden Markov model having observations chosen at least in part from the intermediate states.

Also optionally, at least one statistical model has observations chosen in part from the observation data values and in part from the intermediate state values of another statistical model estimated and provided by the computer.

The invention also relates to a method for detecting at least one scenario from a set of predetermined scenarios wherein a physical system observed by at least one sensor is likely to be found, on the basis of physical system observation data provided by the sensor, comprising the following steps:
receiving a physical system observation data sequence provided by the sensor,
selecting at least one of the scenarios, from the plurality of predetermined scenarios, on the basis of the observation data sequence and at least one statistical model stored in memory and associating possible observation data values with the predetermined scenarios,
and whereby, the memory storing a plurality of statistical models broken down into a plurality of ordered levels, the selection comprises the following steps:
determining intermediate state values on the basis of the observation data sequence and at least one first-level, or input level, statistical model, wherein each statistical model associates possible values of at least a portion of the observation data with specific intermediate states for the statistical model, and
selecting said at least one scenario, on the basis of the intermediate state values and at least one final-level, or output level, statistical model, wherein each statistical model associates possible values of at least a portion of the intermediate states from a lower level with at least a portion of the predetermined scenarios.

Advantageously, this method further comprises the following steps:
determining a sequence of standardised measurement values of at least a portion of the intermediate states based on at least one statistical model defined to determine that portion of the intermediate states and on values received by the statistical model, and selecting said at least one scenario, on the basis of the sequence of standardised measurement values and at least one output level statistical model.

The invention also relates to a computer program suitable for being downloaded from a communication network and/or saved on a computer-readable medium and/or executable by a processor, comprising instructions for executing steps of a method for determining a subject's condition according to the invention, when said program is executed on a computer.

The invention will be understood more clearly using the description hereinafter, given merely as an example, with reference to the appended figures wherein.

Figure 1:
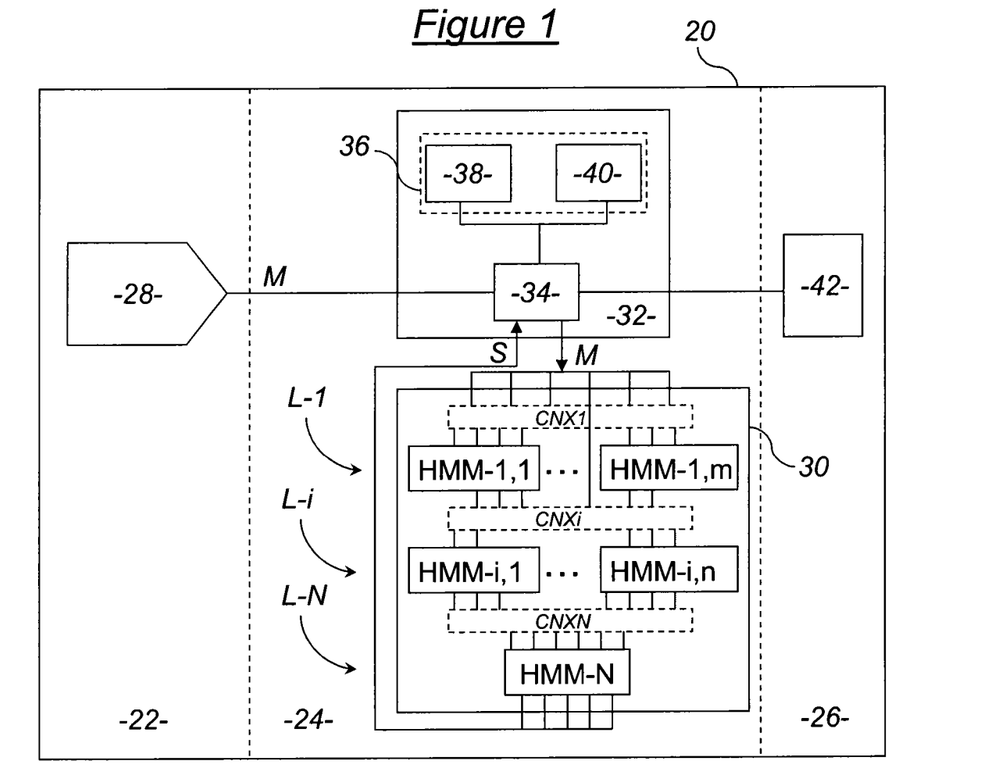
FIG. 1 schematically represents the general structure of a detection device according to a first embodiment of the invention, FIG. 2 schematically represents the general structure of a detection device according to a second embodiment of the invention.

The device 20 represented in FIG. 1 is a device for detecting at least one scenario from a set of predetermined scenarios S-1, ..., S-p wherein a physical system observed by at least one sensor is likely to be found. For this purpose, it comprises an observation module 22, a processing module 24 and an interface module 26.

The observation module 22 comprises one or a plurality of sensors represented by the single reference 28 for observing the physical system.

Some non-limiting examples of sensors and scenarios suitable for being observed using these sensors are given:

the sensor 28 may for example comprise a motion sensor having one, two or three measurement axes, particularly a 3D accelerometer worn by a subject, for determining an epileptic seizure or non-seizure scenario in the subject, the sensor 28 may comprise a motion sensor having one, two or three measurement axes, particularly a 3D accelerometer worn by a subject, for determining the subject's position from a plurality of possible positions liable to occur in succession (for example, reclined, upright/seated, change of position, walking), more generally, it may comprise a motion sensor for determining the activity of a mobile system in a set of predetermined activities, it may comprise a cardiometer for determining a subject's activity or sequence of activities from a plurality of possible activities (for example, rest, start of exertion, short plateau during exertion, long plateau during exertion, end of exertion, short rest), it may comprise a blood glucose sensor for a subject or animal suffering from diabetes for determining an episode or non-episode scenario, it may comprise a pressure sensor for determining the operating status (normal, limit, abnormal) of a pressurised facility at all times, etc.

The sensor 28 may also comprise a plurality of sensors each providing observations which, in combination, are suitable for envisaging detecting more complex scenarios.

It makes measurements on the physical system to provide at least one observation signal, transmitted in the form of a sequence M of observation data to the processing module 24. The observation data may be directly obtained from sampling the observation signal or obtained after one or a plurality of processing operations, particularly one or a plurality of filtering operations, on the signal. It is thus clear that the observation data may be single- or multi-valued, including when only a single sensor 28 is available.

The processing module 24 is an electronic circuit, particularly that of a computer. It comprises storage means 30, for example a RAM, ROM or other memory, wherein statistical model parameters, for example those of hidden Markov models, are stored.

As a general rule, the structured set of these statistical models, stored in memory 30, associates possible observation data values with the predetermined scenarios S-1, ..., S-p.

The processing module 24 further comprises a computer 32, for example a central processing unit equipped with a microprocessor 34 and storage space for at least one computer program 36. This computer 32, and more specifically the microprocessor 34, is connected to the sensor 28 and to the memory 30.

The computer program 36 fulfils two main functions illustrated by modules 38 and 40 in FIG. 1.

The first function, fulfilled by the detection module 38, for example in the form of an instruction loop, is a function for detecting at least one scenario wherein the physical system is found, on receiving a sequence M of observation data provided by the sensor 18. More specifically, the detection module 38 is programmed to enable the microprocessor 34 to select at least one of the scenarios S-1, ..., S-N by processing the sequence M using the structured set of statistical models stored in memory 30.

The second function, fulfilled by the module 40, for example in the form of an instruction loop, is a post-processing function. More specifically, the post-processing module 40 may be programmed to enable the microprocessor 34 to process the result provided by executing the detection module 38, for example by means of Bayesian techniques over clearly defined time periods. In particular, these Bayesian techniques may be based on hidden Markov models according to the first application category mentioned above. The second function is optional and may for example be executed from the end of execution of the first.

The interface module 26 comprises an interface 42 for displaying the result of a detection carried out by the microprocessor 34. Since one of the possible benefits of the detection device 20 is that of detecting a critical scenario from a set of possible scenarios, this interface 42 may particularly comprise an alert trigger. The interface 42 or the alert trigger thereof may for example comprise a screen, for displaying results or a warning message, a speaker, for emitting an audio signal, or an emitter, for transmitting a signal to a remote alarm.

The set of statistical models stored in memory 30 is structured into at least two ordered statistical model levels, between a first level L-1, or input level, and a final level L-N, or output level. In the input level L-1, each statistical model associates possible values of at least a portion of the observation data with specific intermediate states for the statistical model. In particular, when the sequence M of observation data is multi-valued, it may be considered to be a set of a plurality of sequences of observation values, each statistical model of the input level L-1 receiving one or a plurality of these sequences of observation values. This is symbolised in FIG. 1 by the connection interface CNX1 represented as a dotted line between the sequence M of observation data and the input level L-1. In the output level L-N, each statistical model associates possible values of at least a portion of the intermediate states from a lower level with at least a portion of the predetermined scenarios S-1, . . . , S-p. This is symbolised in FIG. 1 by the connection interface CNXN represented as a dotted line at the input of the output level L-N.

According to simple alternative embodiments, the structured set of statistical models stored in memory 30 may only comprise two levels, the input level and the output level. Each statistical model of the output level L-N thus draws the observations thereof from values adopted by intermediate states of input level statistical model(s). These intermediate states are internal states of the structured set stored in memory 30 enabling the statistical modelling of the detection device 20 to act as a buffer between the sequence M of observation data and the decision relating to the scenarios S-1, . . . , S-N.

According to more complex alternative embodiments, as illustrated in FIG. 1, the structured set of statistical models stored in memory 30 may comprise at least three levels, the input level L-1, the output level L-N and at least one further level L-i. Each statistical model of any level L-i associates possible values of at least a portion of the observation data and/or at least a portion of the intermediate states of a lower level with specific intermediate states for the statistical model. This is symbolised in FIG. 1 by the connection interface CNXi represented as a dotted line at the input of the level L-i.

In the first embodiment illustrated in FIG. 1 as a non-limiting example, each statistical model is a hidden Markov model, each level comprises a number of statistical models which may be different from the other levels and the output level L-N comprises a single statistical model. In this way, the input level L-1 comprises m Markov models noted HMM-1,1 to HMM-1,$m$, the level L-i represented comprises n Markov models noted HMM-i,1 to HMM-i,n and the output level L-N comprises a Markov model noted HMM-N.

Any one of these hidden Markov models stored, noted generally as HMM, is defined by the following parameters:
C, the number of hidden states of the model HMM,
$\pi_1, \ldots, \pi_C$, the C initial probabilities, independent of any observation, of each hidden state of the model HMM,
$(a_{i,j})_{1 \leq i,j \leq C}$, the transition probability matrix from each hidden state i to each other hidden state j of the model HMM, and
for each hidden state, the parameters of a probability law of the observation provided at each time at the module input.

As a non-limiting example and to simplify the notations, the probability law of each hidden state i of the model HMM may be chosen in the range of normal laws. In this case, it is defined by the expectation $\mu_i$ thereof and the variance $E\Sigma_i$ thereof. If the input data of the model HMM provided is multi-valued, $\mu_i$ is a vector comprising the same number of components and $\Sigma_i$ a matrix comprising the same number of rows and columns as input values provided at each time of the model HMM.

This first embodiment is in line with the second application category of hidden Markov models mentioned above for detecting scenarios, wherein each hidden state of the model HMM-N of the output level L-N corresponds to one of the scenarios from the set of predetermined scenarios S-1, . . . , S-p. According to this second application category, the microprocessor 34 returns, at the output of the model HMM-N and advantageously by executing the suitable Viterbi algorithm for the scenario, a sequence S of scenarios considered to be the most probable in view of the sequence M of observation data.

Figure 2:
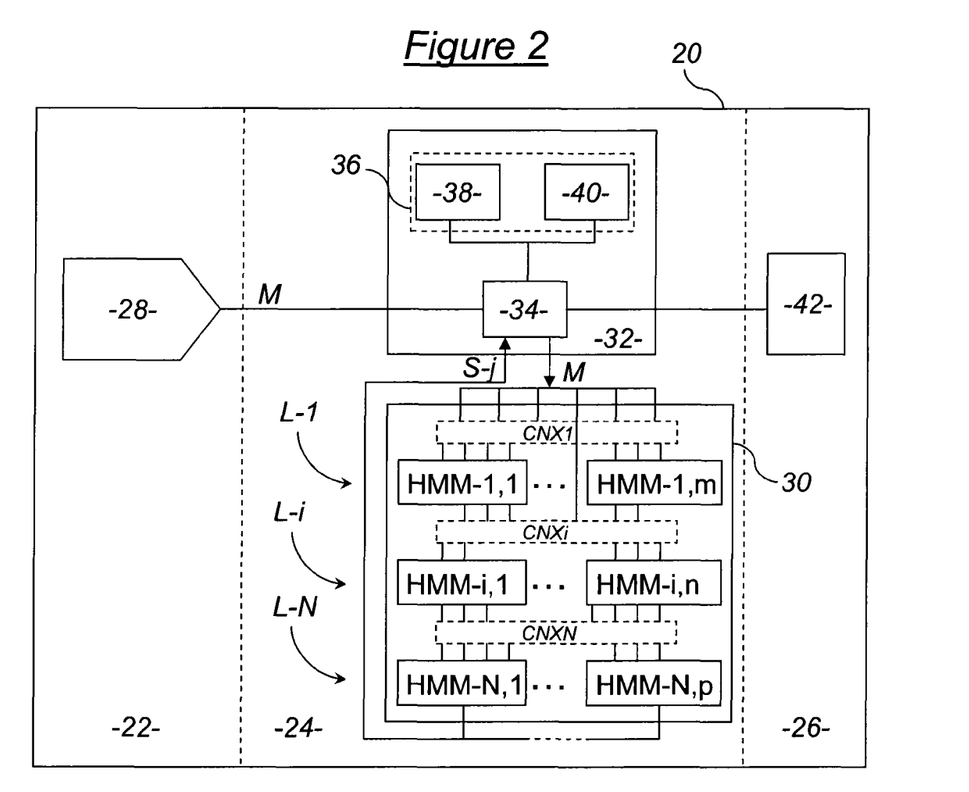

FIG. 2 illustrates a second embodiment wherein the common elements with the first embodiment in FIG. 1 bear the same references and will not be detailed.

This second embodiment differs from the previous embodiment in that the output level L-N comprises a plurality of Markov models, in particular one Markov model per possible predetermined scenario, noted HMM-N,1 to HMM-N, p.

This second embodiment is in line with the first application category of hidden Markov models mentioned above for detecting scenarios, wherein each model HMM-N,1, . . . HMM-N,p of the output level L-N corresponds to one of the scenarios from the set of predetermined scenarios S-1, . . . , S-p, the parameters thereof being predefined to reflect the scenario optimally. According to this first application category, the microprocessor 34 selects, at the output of the level L-N, a scenario S-j considered to be the most representative of the sequence M of observation data. It should be noted that, according to this application category, the hidden states of each statistical model of the output level L-N are not of particular significance.

Optionally, in the two embodiments mentioned above, the statistical Markov models of the levels L-1 to L-(N−1), i.e. all the levels other than the output level L-N, have intermediate states from which it is possible to extract a sequence of standardised values.

In practice, the program 38 executed by the microprocessor 34 is designed for:
determining a sequence of standardised measurement values of at least a portion of the intermediate states of the Markov statistical models of the levels other than the output level L-N, and
selecting the sequence S or the scenario S-j, on the basis of the sequence of standardised measurement values.

As specified above, the term "standardised measurement values" denotes, for a given statistical model, that the sum at each time of the intermediate state measurement values thereof is equal to a time-independent constant.

In this case, the advantage of at least partially preventing some observation parameters provided by the sensor 28 from concealing others, for example merely in that they take values in different scale ranges, is further offered.

Also optionally, the program 38 executed by the microprocessor 34 is designed to determine a sequence of standardised measurement values of all the intermediate states based on all the statistical models defined to determine the intermediate states and on values received by the statistical models. Preferably, the same constant is assigned to all the statistical models in question to equate all the observation parameters.

The standardised values are for example probability values of each of the intermediate states of each model of levels other than the output level L-N as a function of the input values of this model provided. A further advantage of this standardisation, particularly in the form of probabilities, is that of enabling the prior definition of the default values of each of the intermediate states, so as to remedy at least partial or temporary failures of the sensor 28.

Finally, it should be noted that this standardisation option is not dependent on the nature of the statistical models used. In the case of Markov models wherein the outputs suitable for processing by the output level are hidden states of the models of lower levels, the standardisation option applies to these hidden states. However, more generally, this standardisation option applies to the outputs of statistical models of lower levels processed by the output level, wherein these outputs are deemed to be intermediate states.

An intermediate state probability calculation will now be detailed in the specific but non-limiting case of hidden Markov models.

HMM denotes the generic notation of one of the statistical models of one of the levels other than the output level, $Y_n$ the statistical process representing an input data sequence of the model HMM provided and $X_n$ the statistical process corresponding to the most suitable hidden state sequence for the input data sequence. It is further assumed that the variable $Y_n$ is independent of $Y_{n-1}$ conditionally to $X_n$. This assumption, which is conventional in respect of signal processing using hidden Markov models, makes it possible to express the following known relation:

$$p(X_{0:N}, Y_{0:N}) = p(X_0)p(Y_0 \mid X_0) \prod_{l=1}^{N} p(Y_l \mid X_l)p(X_l \mid X_{l-1}), \quad (1)$$

where 0:N is a sequence sampled between the times 0 and N.

As mentioned above, it is sought to determine a sequence of standardised measurement values of the hidden states of the model HMM on the basis of the input data sequence of the model, particularly by means of a probability sequence calculation.

For each hidden state Ei of the model HMM, $p(X_N=i \mid Y_{0:N})$ denotes the probability at the time N in the light of the sequence $Y_{0:N}$.

This probability is calculated as follows:

$$p(X_N = i \mid Y_{0:N}) = p(X_N = i, Y_{0:N}) / p(Y_{0:N}) = \quad (2)$$

$$\frac{1}{p(Y_{0:N})} \sum_{X_0, \ldots, X_{N-1}} p(X_{0:N-1}, X_N = i, Y_{0:N}).$$

Using equation (1), equation (2) becomes:

$$p(X_N = i \mid Y_{0:N}) = \frac{1}{p(Y_{0:N})} \sum_{X_0, \ldots, X_{N-1}} p(X_0)p(Y_0 \mid X_0) \prod_{l=1}^{N-1} p_l, \text{ where} \quad (3)$$

$$p_l = p(Y_l \mid X_l)p(X_l \mid X_{l-1})p(Y_N \mid X_N = i)p(X_N = i \mid X_{N-1}).$$

Now let us introduce the variable $\alpha_0(i) = p(X_0=i)p(Y_0 \mid X_0=i)$ and the series $\alpha_n(i)$ defined by:

$$p(X_N = i \mid Y_{0:N}) = \quad (5)$$

$$\frac{1}{p(Y_{0:N})} \alpha_N(i) = \frac{\alpha_N(i)}{\sum_i \alpha_N(i)} \text{ since the sum of the probabilites equals 1.}$$

It can thus be shown that the probability $p(X_N=i \mid Y_{0:N})$ is expressed as follows as a function of the series $\alpha_n(i)$:

$$\alpha_n(i) = \sum_j \alpha_{n-1}(j)p(Y_n \mid X_n = i)p(X_n = i \mid X_{n-1} = j). \quad (4)$$

The probability $p(X_N=i \mid Y_{0:N})$ can thus be calculated iteratively using equations (4) et (5). Indeed, these equations define a recurrence relation between successive values of the sequence of probability values $p(X_N=i \mid Y_{0:N})$. Furthermore, it is observed that this recurrence relation involves a single value, dependent on the recurrence index, of the input data sequence provided: more specifically, it consists of the last input data item provided at the iteration N, $Y_N$, which should be known to determine the values of $p(Y_N \mid X_N=i)$ in the expression of $\alpha_N(i)$.

However, in practice, numerical convergence problems may arise and it is preferred to use the following equivalent equations:

Initialisation:

$$\tilde{p}(X_0 = i \mid Y_0) = p(X_0 = i)p(Y_0 \mid X_0 = i),$$

$$p(X_0 = i \mid Y_0) = \frac{\tilde{p}(X_0 = i \mid Y_0)}{\sum_j \tilde{p}(X_0 = j \mid Y_0)} \text{(standardised value).}$$

Recurrence on N:

$$\tilde{p}(X_{N+1} = i \mid Y_{0:N+1}) =$$

$$\sum_j p(X_N = j \mid Y_{0:N})p(Y_{N+1} \mid X_{N+1} = i)p(X_{N+1} = i \mid X_N = j),$$

$$p(X_{N+1} = i \mid Y_{0:N+1}) = \frac{\tilde{p}(X_{N+1} = i \mid Y_{0:N+1})}{\sum_j \tilde{p}(X_{N+1} = j \mid Y_{0:N+1})} \text{(standardised value).}$$

These recurrence equations are equivalent to equations (4) and (5) because $p(X_N=i \mid Y_{0:N})$ is proportional to $\alpha_n(i)$ and this proportionality coefficient is governed by the standardisation requiring the sum of the probabilities to equal 1.

It should be noted that the observation 22, processing 24 and interface 26 modules are structurally separable. In this way, the detection device 20 may be designed in one piece or a plurality of separate material elements interconnected by wired or wireless data transmission means. In particular, the processing 24 and optionally interface 26 modules may be implemented by a computer. Only the observation module 22 is necessarily in the vicinity of or in contact with the physical system observed since it comprises the sensor(s).

Figure 3:
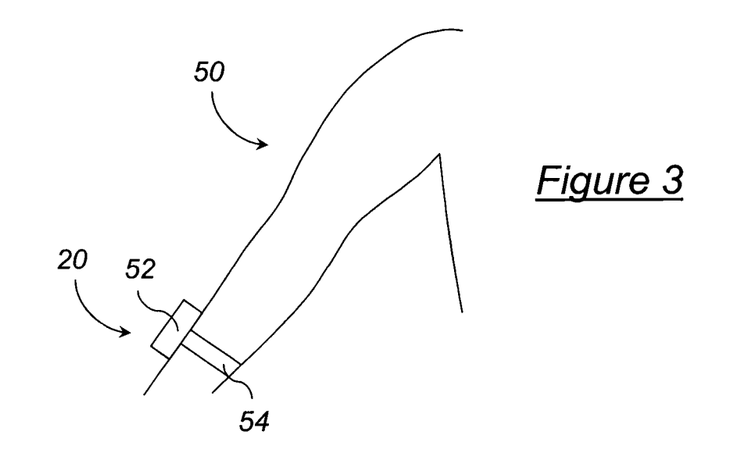
FIG. 3 illustrates a particular use of the detection device in FIG. 1 or 2.

In FIG. 3, a particularly compact embodiment is illustrated, for an application for monitoring a subject 50. According to this embodiment, the detection device 20 in FIG. 1 or 2 is fully integrated in a unit 52 worn by the subject. The sensor is for example a 3D accelerometer and the scenarios observed are for example three in number as in the particular example detailed hereinafter with reference to FIGS. 5 and 6: a "reclined" state, "an upright/seated" state and a "moving" state of the subject 50, each of these states being represented by a hidden state corresponding to a single Markov model of the output level L-N. For this application, the unit 52 is for example firmly secured onto one of the subject's 50 arms by means of a wrist strap 54, such that the detection device 20 is worn like a watch. More appropriately for this application, the unit 52 may be secured to the subject's 50 waist using a belt.

Figure 4:
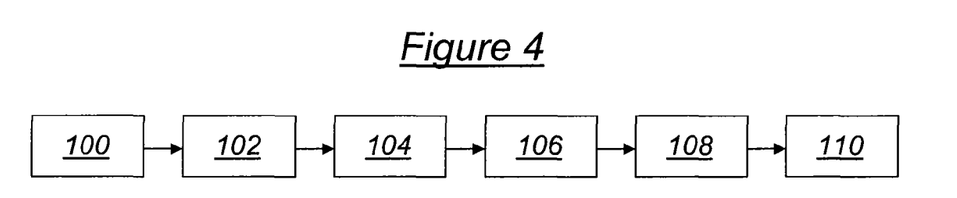
FIG. 4 illustrates the successive steps of a detection method according to one embodiment of the invention, FIGS. 5, 6, 7 and 8 schematically represent various possible arrangements of statistical models stored in the detection device in FIG. 1 or 2, for a first application, FIG. 9 schematically represents a possible arrangement of statistical models stored in the detection device in FIG. 1 or 2, for a second application.

The operation of the detection device 20 will not be detailed with reference to FIG. 4. More specifically, the execution of the detection module 38 and the post-processing module 40 by the microprocessor 34 generates the sequence of steps illustrated in this figure.

During a first step 100, the sensor 28 (or sensors in the case of a plurality of sensors) transmits a sequence M of observation data to the computer 32. This data is for example multi-valued such that the data sequence is actually a union of observation value sequences, wherein each sequence of values is obtained from a sensor or a specific processing operation on a signal provided by a sensor.

During one step 102, during the reception 100 of the successive data transmitted by the sensor 28, the microprocessor 34 of the computer 32 runs the execution of the detection software module 38.

During the next step 104, the hidden state probability values of the statistical models of the input level L-1 are successively determined on the basis of the sequence of observation data and the input level statistical models.

During the next step 106, the hidden state probability values of the statistical models of the level(s) L-i are successively determined on the basis of the hidden state probability values of the statistical models of one or a plurality of lower levels, optionally also on a portion of the sequence of observation data and the statistical models of the level L-i.

During a step 108, a sequence S of scenarios, or a scenario S-j whereby the device 20 implements the first or second embodiment, is selected on the basis of the hidden state probability values of the statistical models of one or plurality of lower level(s) and the statistical model(s) of the output level L-N.

Finally, during a step 110, post-processing may be optionally carried out by the microprocessor 34 by executing the module 40 on one or a plurality of results of the step 108.

It is thus clear that the detection device 20 described above is capable of determining, on the basis of a sequence M of observation data, a sequence of intermediate state values of the statistical models of levels other than the output level L-N, preferably even a sequence of standardised values such as probabilities, and determining, on the basis of this sequence of intermediate state values, the scenario or sequence of scenarios representing the observation sequence M, using the statistical models or statistical model of the output level, respectively.

A first concrete example, according to the second application category, will be described hereinafter with reference to FIG. 5.

According to this example, the sensor 28 comprises a motion sensor having one, two or three measurement axes, particularly a 3D accelerometer worn by a subject, in the chest area. The 3D accelerometer provides a vector signal which is filtered and sampled to produce:

firstly, a sequence O1 of observation values combining low-frequency components of the vector signal and forming a mean component of this vector signal representing an orientation of the sensor 28 with respect to the ground, secondly, a sequence O2 of observation values combining high-frequency components of the vector signal and forming a variance component of this vector signal representing a dynamic range of the sensor 28 with respect to the ground.

In practice and in this example of application, the low-frequency components consist of frequencies less than a few Hertz, for example less than 2 Hz. The high-frequency components consist of frequencies greater than a few Hertz, for example greater than 2 Hz.

At a first input level, the parameters of a hidden Markov model HMM-A are stored in the memory 30. This Markov model HMM-A is intended to receive, at the input, the sequence of values O1 and the microprocessor 34 is designed to provide, at the output of the model HMM-A, two sequences of probability values of two hidden states A1 and A2. The initial probabilities, the transition probability matrix and the probability laws of the states A1 and A2 are defined and stored in memory 30, for this Markov model HMM-A, such that the hidden state A1 represents a "reclined" position model and the hidden state A2 represents an "upright upper body" position model for the subject wearing the detection device 20. It is the task of those skilled in the art, in a manner known per se, to define these parameters so that the statistical model HMM-A optimally corresponds to the position model sought for the subject. It is particularly possible to model the probability laws of the states A1 and A2 with normal average laws corresponding to the averages of the values of the sequence O1 when the subject is reclined for the state A1 and when the upper body is upright for the state A2.

Also at this input level, the parameters of a hidden Markov model HMM-B are stored in the memory 30. This Markov model HMM-B is intended to receive, at the input, the sequence of values O2 and the microprocessor 34 is designed to provide, at the output of the model HMM-B, two sequences of probability values of two hidden states B1 and B2. The initial probabilities, the transition probability matrix and the probability laws of the states B1 and B2 are defined and stored in memory 30, for this Markov model HMM-B, such that the hidden state B1 represents a "static" dynamic model and the hidden state B2 represents a "moving" dynamic model for the subject wearing the detection device 20. It is the task of those skilled in the art, in a manner known per se, to define these parameters so that the statistical model HMM-B optimally corresponds to the dynamic model sought for the subject. It is particularly possible to model the probability laws of the states B1 and B2 with $\chi_2$ laws with parameters dependent on the state in question.

At a second output level, the parameters of a hidden Markov model HMM-C are stored in the memory 30. This Markov model HMM-C is intended to receive, at the input, the sequences of probability values of the states A1, A2, B1 and B2 and the microprocessor 34 is designed to provide, at the output of the model HMM-C, a sequence of scenarios chosen from a "reclined" scenario represented by a first hidden state C1 of HMM-C, an "upright/seated" scenario represented by a second hidden state C2 of HMM-C and a "moving" scenario represented by a third hidden state C3 of HMM-C. The initial probabilities, the transition probability matrix and the probability laws of the states C1, C2 and C3 are defined and stored in memory 30, so that this Markov model HMM-C represents the three scenarios mentioned above realistically. It is the task of those skilled in the art, in a manner known per se, to define these parameters so that the statistical model HMM-C optimally corresponds to the scenario determination model sought for the subject.

Figure 5:
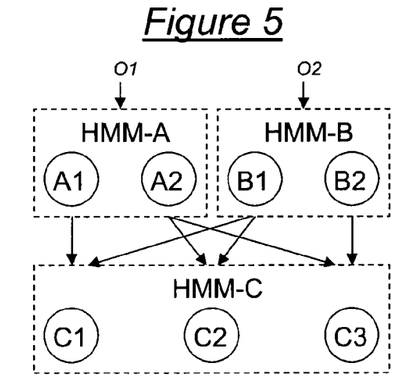

It is further noted that, in the example in FIG. 5, the statistical models HMM-A and HMM-B are independent and on the same level, each making an equitable contribution to the model HMM-C.

Moreover, in this example, the probability of the hidden state C1 is defined as dependent on the probabilities of the hidden states A1 and B1. Consequently, due to the independence of the statistical models HMM-A and HMM-B, the probability of the hidden state C1 is estimated directly on the basis of the product of the probabilities of the hidden states A1 and B1. The probability of the hidden state C2 is defined as dependent on the probabilities of the hidden states A2 and B1. Consequently, due to the independence of the statistical models HMM-A and HMM-B, the probability of the hidden state C2 is estimated directly on the basis of the product of the probabilities of the hidden states A2 and B1. Finally, the probability of the hidden state C3 is defined as dependent on the probabilities of the hidden states A2 and B2. Consequently, due to the independence of the statistical models HMM-A and HMM-B, the probability of the hidden state C3 is estimated directly on the basis of the product of the probabilities of the hidden states A2 and B2.

One limitation of this simple example wherein the two statistical models HMM-A and HMM-B are independent and on the same level is that, if the sensor 28 moves while the subject is reclined, the detection device 20 will not be able to make a decision (scenario C1 or C3?).

Figure 6:
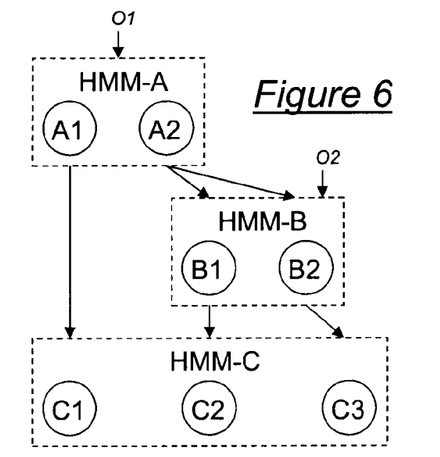

A second concrete example for the same application as the first is illustrated in FIG. 6. The sensor 28 is identical to that in the previous example and provides the same sequences of observation values O1 and O2.

At a first input level, the parameters of the hidden Markov model HMM-A mentioned above are stored in the memory 30.

At a second intermediate level, the parameters of the hidden Markov model HMM-B mentioned above are stored in the memory 30. However, in this second example, the microprocessor 34 is designed to provide, at the output of the model HMM-B, two sequences of probability values of two hidden states B1 and B2 dependent on the sequence of probability values of the hidden state A2. The statistical model HMM-B is thus dependent on the model HMM-A in this second example.

At a third output level, the parameters of the hidden Markov model HMM-C mentioned above are stored in the memory 30. However, in this second example, the probability of the hidden state C1 is defined as dependent on the probability of the hidden state A1 alone. The probability of the hidden state C2 is defined as dependent on the probability of the hidden state B1 alone. Consequently, due to the dependence of the statistical models HMM-A and HMM-B, the probability of the hidden state C2 is estimated directly on the basis of the probability of the hidden state B1 if the probability of A2 is the highest of the hidden states of HMM-A, and as zero otherwise. Finally, the probability of the hidden state C3 is defined as dependent on the probability of the hidden state B2 alone. Consequently, due to the dependence of the statistical models HMM-A and HMM-B, the probability of the hidden state C3 is estimated directly on the basis of the probability of the hidden state B2 if the probability of A2 is the highest of the hidden states of HMM-A, and as zero otherwise.

Unlike the previous example, in this second example, if the sensor 28 moves while the subject is reclined, the detection device 20 will decide that the subject is reclined (scenario C1).

One drawback of the first and second examples mentioned above is that the dynamic model HMM-B has non-time-constrained hidden states, i.e. either a "static" state, or a "moving" state. It may be sought to refine these applications by providing a non-stationary statistical model, comprising for example a "static" state, a "moving for less than x seconds" state and a "moving for at least x seconds" state. One solution to arrive at this result while retaining hidden Markov modelling is that of defining a Markov model with numerous virtual hidden states, such as "moving for 1 clock tick", "moving for 2 clock ticks", . . . , "moving for N clock ticks" and grouping some virtual hidden states into a real hidden state wherein the parameters are derived from those of the virtual hidden states.

Figure 7:
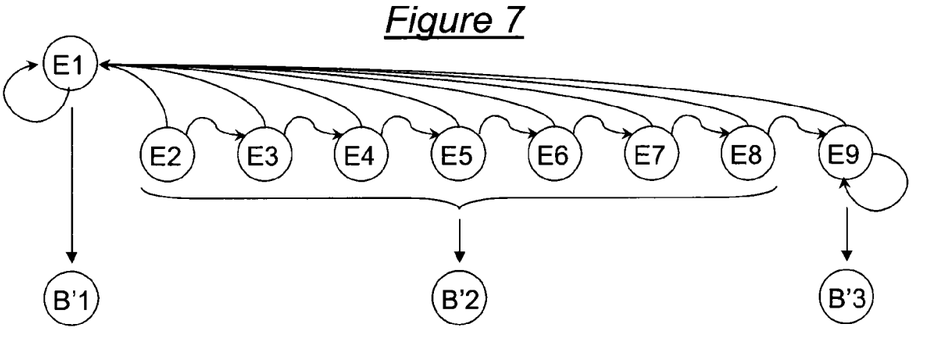
Figure 8:
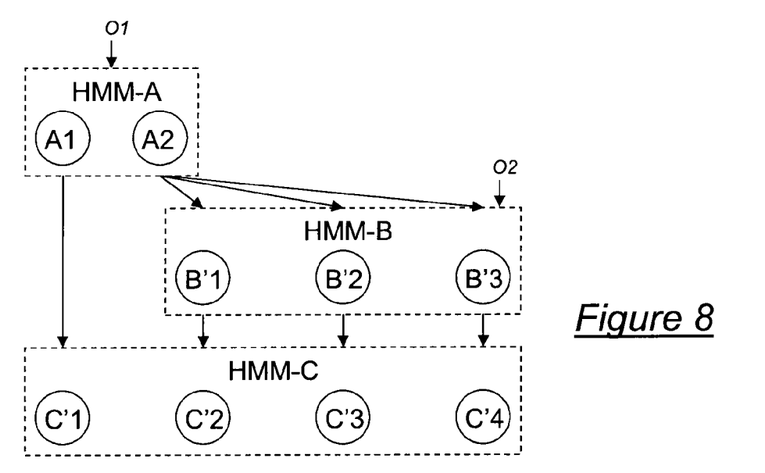

A third concrete example for the same application as the first and the second is illustrated in FIG. 8 and the principle thereof is represented schematically in FIG. 7. The sensor 28 is identical to that in the previous example and provides the same sequences of observation values O1 and O2.

As illustrated in FIG. 7, the model HMM-B is refined so as to have three hidden states: the hidden state B'1, identical to B1, represents a "static" dynamic model, the hidden state B'2 represents a "moving for less than 8 clock ticks" dynamic model and the hidden state B'3 represents a "moving for at least 8 clock ticks" dynamic model. For this, these three states are derived from 9 virtual hidden states E1 to E9.

The virtual state E1 corresponds to the hidden state B'1. This state is not time-constrained.

The virtual states E2 to E9 are time-constrained states corresponding to the two hidden states B'2 and B'3. If $V_n$ denotes the random variable of these virtual states, $X_n$ the random output variable of the model HMM-B and $Y_n$, the random input variable of the model HMM-B, given that it is further possible to return to the virtual state E1 of any virtual state, this gives:

$$\forall i \in [2, 8], p(V_n = Ei \mid V_{n-1} = Ej) = \begin{cases} 1 & si\ i = j+1 \\ 1 & si\ i \neq j+1, \end{cases}$$

$$p(V_n = E9 \mid V_{n-1} = Ej) = \begin{cases} \lambda & si\ j = 8 \\ 1-\lambda & si\ j = 9 \\ 0 & si\ j \in [2, 7], \end{cases}$$

$$\forall i \in [2, 9], p(Y_n \mid V_{n-1} = Ei) = p(Y_n \mid V_{n-1} = E2), \text{ and}$$

$$p(X_n = B'1) = p(V_n = E1),$$

$$p(X_n = B'2) = \sum_{i=2}^{8} p(V_n = Ei),$$

$$p(X_n = B'3) = p(V_n = E9).$$

These equations are suitable for easy generalisation to a set comprising both non-time-constrained hidden states and time-constrained hidden states dependent on the same probability density of the vector observed.

The structured set of models illustrated in FIG. 8 results from the principle represented in FIG. 7.

The first input level of this third example is identical to the input level of the second example.

At the second intermediate level, the model HMM-B is suitable as mentioned above for having the three hidden states B'1, B'2 and B'3. The microprocessor 34 is designed to provide, at the output of this suitable model HMM-B, three sequences of probability values of the three hidden states B'1, B'2 and B'3 dependent on the sequence of probability values of the hidden state A2.

At the third output level, the model HMM-C is suitable for having four hidden states C'1, C'2, C'3 and C'4: C'1 represents a "reclined" scenario, C'2 an "upright/seated" scenario, C'3 a "change of position" scenario and C'4 a "walking" scenario. The probability of the hidden state C'1 is defined as dependent on the probability of the hidden state A1 alone. The probability of the hidden state C'2 is defined as dependent on the probability of the hidden state B'1 alone. Consequently, due to the dependence of the statistical models HMM-A and HMM-B, the probability of the hidden state C'2 is estimated directly on the basis of the probability of the hidden state B'1 if the probability of A2 is the highest of the hidden states of HMM-A, and as zero otherwise. The probability of the hidden state C'3 is defined as dependent on the probability of the hidden state B'2 alone. Consequently, due to the dependence of the statistical models HMM-A and HMM-B, the probability of the hidden state C'3 is estimated directly on the basis of the probability of the hidden state B'2 if the probability of A2 is the highest of the hidden states of HMM-A, and as zero otherwise. Finally, the probability of the hidden state C'4 is defined as dependent on the probability of the hidden state B'3 alone. Consequently, due to the dependence of the statistical models HMM-A and HMM-B, the probability of the hidden state C'4 is estimated directly on the basis of the probability of the hidden state B'3 if the probability of A2 is the highest of the hidden states of HMM-A, and as zero otherwise.

In this way, it is noted that accounting for a time constraint in the model HMM-B enables, at the output, to distinguish between the "change of position" scenario and the "walking" scenario", which was not the case in the first two examples.

Moreover, the three examples mentioned above make it possible to envisage specific post-processing to make a more precise decision on the scenario C2=C'2="upright/seated". The aim of this post-processing operation may be that of measuring whether the signal of the 3D accelerometer has a lower variance less than a predetermined threshold, whereby the subject, who is not making any movement, may be considered to be seated, or whether the signal of the 3D accelerometer has a higher variance greater than the predetermined threshold, whereby the subject, retaining balance at all times, may be considered to be upright. This post-processing may be performed on the basis of hidden Markov modelling according to the first application category mentioned above.

A fourth concrete example, according to the second application category, will now be described with reference to FIG. 9.

According to this example, the sensor 28 comprises a cardiometer worn by a subject. The cardiometer provides a signal representing the subject's heart beats. This signal is processed and sampled to produce:
- firstly, a sequence O1 of observation values obtained by sampling the heart beat signal, representing the subject's heart rate at all times,
- secondly, a sequence O2 of observation values obtained by sampling the differential of the heart beat signal, representing the progression of the subject's heart rate at all times.

At a first input level, the parameters of a hidden Markov model HMM-D are stored in the memory 30. This Markov model HMM-D is intended to receive, at the input, the sequence of values O1 and the microprocessor 34 is designed to provide, at the output of this model HMM-D, two sequences of probability values of two hidden states D1 and D2. The initial probabilities, the transition probability matrix and the probability laws of the states D1 and D2 are defined and stored in memory 30, for this Markov model HMM-D, such that the hidden state D1 represents a "resting" heart rate model and the hidden state D2 represents an "elevated" heart rate model for the subject wearing the detection device 20. It is the task of those skilled in the art, in a manner known per se, to define these parameters so that the statistical model HMM-D optimally corresponds to the position model sought for the subject. It is particularly possible to model the probability laws of the state D1 with a normal law of average 80 and variance 20 and model the probability law of the state D2 with a normal law of average 140 and variance 30.

Also at this input level, the parameters of a hidden Markov model HMM-G are stored in the memory 30. This Markov model HMM-G is intended to receive, at the input, the sequence of values O2 and the microprocessor 34 is designed to provide, at the output of the model HMM-G, four sequences of probability values of four hidden states G1, G2, G3 and G4. The initial probabilities, the transition probability matrix and the probability laws of the states G1, G2, G3 and G4 are defined and stored in memory 30, for this Markov model HMM-G, such that the hidden state G1 represents a "downward" heart rate trend model, the hidden state G2 represents a "constant for less than 10 seconds" heart rate trend model, the hidden state G3 represents a "constant for at least 10 seconds" heart rate trend model and the hidden state G4 an "upward" heart rate trend model for the subject wearing the detection device 20. It is the task of those skilled in the art, in a manner known per se, to define these parameters so that the statistical model HMM-B optimally corresponds to the dynamic model sought for the subject. It is particularly possible to model the probability laws of the state G1 with a normal law of average −5 and variance 3, model the probability laws of the state G2 constrained to last for less than 10 seconds with a normal centred law of variance 3, model the probability laws of the state G3 constrained to last for at least 10 seconds with a normal centred law of variance 3 and model the probability law of the state G4 with a normal law of average 5 and variance 3.

At a second output level, the parameters of a hidden Markov model HMM-F are stored in the memory 30. This Markov model HMM-F is intended to receive, at the input, the sequences of probability values of the states D1, D2, G1, G2, G3 and G4 and the microprocessor 34 is designed to provide, at the output of the model HMM-F, a sequence of scenarios chosen from a "resting" scenario represented by a first hidden state F1 of HMM-F, a "start of exertion" scenario represented by a second hidden state F2 of HMM-F, a "short exertion plateau" scenario represented by a third hidden state F3 of HMM-F, a "long exertion plateau" scenario represented by a fourth hidden state F4 of HMM-F, an "end of exertion" scenario represented by a fifth hidden state F5 of HMM-F and a "short rest" scenario represented by a sixth hidden state F6 of HMM-F. The initial probabilities, the transition probability matrix and the probability laws of the states F1, F2, F3, F4, F5 and F6 are defined and stored in memory 30, so that this Markov model HMM-F represents the six scenarios mentioned above realistically. It is the task of those skilled in the art, in a manner known per se, to define these parameters so that the statistical model HMM-F optimally corresponds to the scenario determination model sought for the subject.

Figure 9:
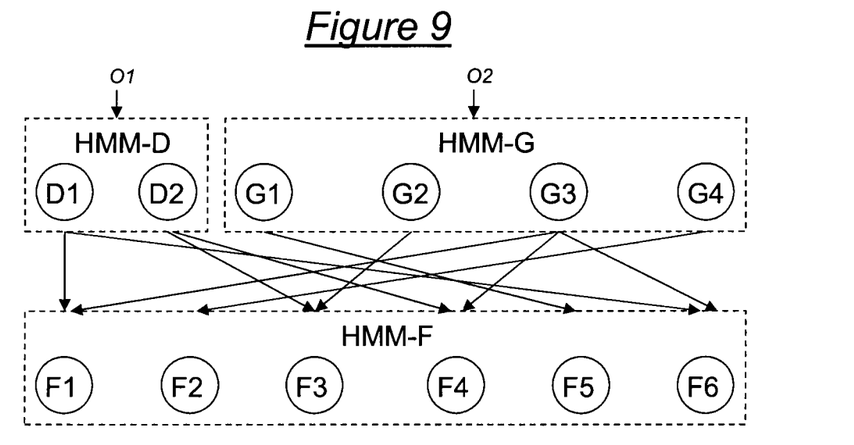

It is further noted that, in the example in FIG. 9, the statistical models HMM-D and HMM-G are independent and on the same level, each making an equitable contribution to the model HMM-F.

Moreover, in this example, the probability of the hidden state F1 is defined as dependent on the probabilities of the hidden states D1 and G3. Consequently, due to the independence of the statistical models HMM-D and HMM-G, the probability of the hidden state F1 is estimated directly on the basis of the product of the probabilities of the hidden states D1 and G3. The probability of the hidden state F2 is defined as dependent on the probability of the hidden state G4 alone. The probability of the hidden state F3 is defined as dependent on the probabilities of the hidden states D2 and G2. Consequently, due to the independence of the statistical models HMM-D and HMM-G, the probability of the hidden state F3 is estimated directly on the basis of the product of the probabilities of the hidden states D2 and G2. The probability of the hidden state F4 is defined as dependent on the probabilities of the hidden states D2 and G3. Consequently, due to the independence of the statistical models HMM-D and HMM-G, the probability of the hidden state F4 is estimated directly on the basis of the product of the probabilities of the hidden states D2 and G3. The probability of the hidden state F5 is defined as dependent on the probability of the hidden state G1 alone. Finally, the probability of the hidden state F6 is defined as dependent on the probabilities of the hidden states D1 and G3. Consequently, due to the independence of the statistical models HMM-D and HMM-G, the probability of the hidden state F6 is estimated directly on the basis of the product of the probabilities of the hidden states D1 and G3.

Figure 10:
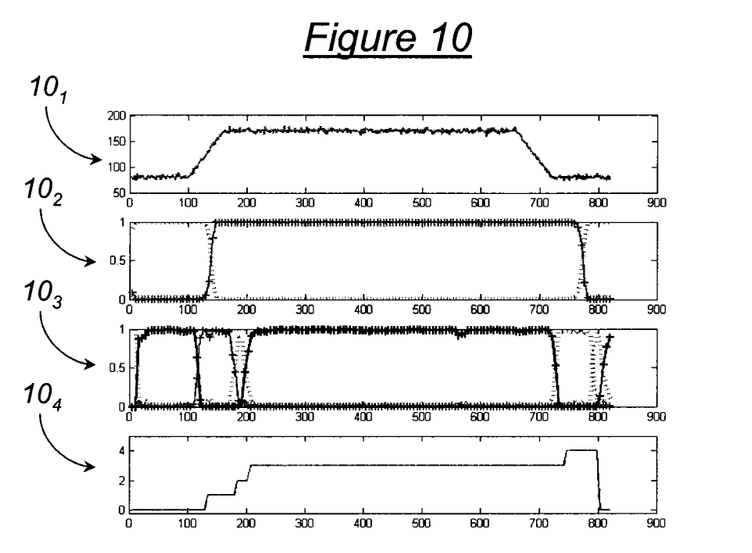
FIG. 10 illustrates, using diagrams, the operation of the device in FIG. 1 or 2 for the second application in FIG. 9.

FIG. 10 illustrates, using diagrams, an operation of the detection device 20 in the context of this fourth example. The diagram $10_1$ represents an example of a heart beat time signal provided by the cardiometer 28. The diagram $10_2$ illustrates the corresponding probability sequences of the hidden states D1 and D2. The diagram $10_3$ illustrates the corresponding probability sequences of the hidden states G1, G2, G3 and G4. Finally, the diagram $10_4$ provides the corresponding sequence of scenarios chosen from the hidden states F1 to F6.

It is clear that a device for detecting scenarios such as described above is suitable for envisaging enhanced performances and flexibility in that the observation data is only indirectly associated with the scenarios suitable for being detected by the device. Adding or removing a sensor thus only has a relative impact on the modelling whereon the detection device is based, with only an input level statistical model being affected. It is particularly possible to define a specific input level statistical model (or set of statistical models) for each sensor.

The possibility of assigning default values to the intermediate states makes it possible to further enhance the robustness of the device.

Moreover, it should be noted that the invention is not limited to the embodiments described above.

In particular, many applications other than those described above can be envisaged according to the sensors used and the models defined.

For example, such a device could also be used to monitor a subject's blood glucose level and prevent or detect episode scenarios without delay. In this specific case, a number of elements are important for triggering hypo- or hyper-glycaemia alarms.

A first point is obviously that of continuously measuring the subject's blood glucose level using a sensor. If this level exceeds a certain limit, it is necessary to alert the subject of the risk incurred. A second point is that of measuring the blood glucose level trend. A slightly elevated level with a low upward trend is less risky that a moderate/higher level with a high upward trend. The models given in the examples mentioned above could thus be very suitable for this application with two input level models:
 a first Markov model using a blood glucose level evaluation, with five hidden states: very low, low, normal, high, very high blood glucose,
 a second Markov model using an evaluation of the progression of the blood glucose level, with three hidden states: downward trend, constant trend, upward trend.

Moreover, the number of input level or intermediate level models could be increased by increasing the number of sensors.

A single output level model could have five hidden states corresponding to five scenarios to be detected:
 "hyperglycaemia requiring treatment": very high blood glucose,
 "hyperglycaemic risk requiring monitoring": high blood glucose with an upward trend,
 "no anomaly detected": elevated but constant or normal or low and constant blood glucose,
 "hypoglycaemic risk requiring monitoring": low blood glucose with a downward trend,
 "hypoglycaemia requiring treatment": very low blood glucose.

It would be obvious for those skilled in the art that various modifications may be made to the embodiments described above, in the light of the teaching disclosed herein. In the claims hereinafter, the terms used should not be interpreted as limiting the claims to the embodiments disclosed in the present description, but should be interpreted to include any equivalents intended to be covered by the claims due to the wording thereof and suitable for being envisaged by those skilled in the art by applying their general knowledge to the implementation of the teaching disclosed herein.

The invention claimed is:

1. A device detecting at least one scenario from a set of predetermined scenarios wherein a physical system observed by at least one sensor is likely to be found, on the basis of physical system observation data provided by the sensor, comprising:
 at least one sensor providing a physical system observation data sequence;
 a memory for storing at least one statistical model associating possible observation data values with the predetermined scenarios;
 circuitry, connected to the sensor and the memory, programmed to select at least one of the scenarios, from the plurality of predetermined scenarios, based on the observation data sequence and the at least one statistical model;
 wherein the memory stores a plurality of statistical models broken down into a plurality of ordered levels between:
  a first level, or input level, wherein each statistical model associates possible values of at least a portion of the observation data with intermediate states that are specific to said each statistical model; and
  a final level, or output level, wherein each statistical model associates possible values of at least a portion of the intermediate states of at least one statistical model of a lower level with at least a portion of the predetermined scenarios;
 wherein the circuitry is further programmed to:
  determine a sequence of standardized measurement values of at least a portion of the intermediate states based on at least one statistical model specifically defined to determine that portion of the intermediate states and on values received by said at least one statistical model, wherein measurement values of an intermediate state suitable for being determined by a given statistical model are standardized when the sum of the measurement values of all the intermediate states suitable for being determinable by the given statistical model and at the same time is equal to a predetermined time-independent constant; and
  select the at least one scenario, on the basis of the sequence of standardized measurement values and at least one output level statistical model,
 wherein each statistical model of a level other than the output level has intermediate states from each of which the output is at least part of the sequence of standardized measurement values by imposing that the sum at each time of the intermediate state measurement values of each statistical model of a level other than the output level is equal to a time-independent constant, and the output level determines directly from the outputted sequences of standardized measurement values either one of the scenarios which is selected among the predetermined scenarios or a sequence of scenarios from among the predetermined scenarios.

2. A detection device according to claim 1, wherein the circuitry is further programmed to determine the sequence of standardized measurement values of all the intermediate states based on all the statistical models defined to determine the intermediate states and on values received by the statistical models.

3. A detection device according to claim 1, wherein the standardized measurement values are probability values.

4. A detection device according to claim 3, wherein at least one statistical model of a level other than the output level is a hidden Markov model, and wherein the circuitry is further programmed to determine a sequence of probability values of at least a portion of the hidden states thereof iteratively on the basis of a data sequence provided at the input of the Markov model according to a recurrence relation between successive values of the probability value sequence, the recurrence relation involving a single value, dependent on the recurrence index, of the input data sequence provided.

5. A detection device according to claim 4, wherein the recurrence relation takes a form of:

INITIALIZATION:

$$\tilde{p}(X_0 = i | Y_0) = p(X_0 = i)p(Y_0 | X_0 = i) \text{ and}$$

$$p(X_0 = i | Y_0) = \frac{\tilde{p}(X_0 = i | Y_0)}{\sum_j \tilde{p}(X_0 = j | Y_0)},$$

RECURRENCE ON N:

$$\tilde{p}(X_{N+1} = i | Y_{0:N+1}) =$$

$$\sum_j p(X_N = j | Y_{0:N})p(Y_{N+1} | X_{N+1} = i)p(X_{N+1} = i | X_N = j) \text{ and}$$

$$p(X_{N+1} = i | Y_{0:N+1}) = \frac{\tilde{p}(X_{N+1} = i | Y_{0:N+1})}{\sum_j \tilde{p}(X_{N+1} = j | Y_{0:N+1})},$$

wherein i represents the hidden state index in question, j represents another hidden state index, N the sequence index, Y the statistical process representing the input data sequence provided, X the statistical process corresponding to the most suitable hidden state sequence for the input data sequence.

6. A detection device according to claim 1, wherein:
the output level comprises a Markov statistical model wherein the hidden states correspond to the predetermined scenarios, and wherein the observations are chosen from estimated intermediate state values provided by the circuitry; and
the circuitry is further programmed to output a sequence of scenarios, wherein each is selected from the predetermined scenarios, on the basis of the sequence of intermediate state values and the output level Markov statistical model.

7. A detection device according to claim 1, wherein:
the output level comprises a hidden Markov statistical model for each scenario from the set of predetermined scenarios, and wherein the observations are chosen from estimated intermediate state values provided by the circuitry; and
the circuitry is further programmed to select an output level Markov model on the basis of the sequence of intermediate state values and to output the corresponding scenario.

8. A detection device according to claim 1, wherein at least one statistical model of a different level to the input level and the output level is a hidden Markov model having observations chosen at least in part from the intermediate states.

9. A detection device according to claim 1, wherein at least one statistical model has observations chosen in part from the observation data values and in part from the intermediate state values of another statistical model estimated and provided by the circuitry.

10. A method, implemented by a detection device, for detecting at least one scenario from a set of predetermined scenarios wherein a physical system observed by at least one sensor is likely to be found, on the basis of physical system observation data provided by the sensor, comprising:
receiving a physical system observation data sequence provided by the sensor;
selecting at least one of the scenarios, from the plurality of predetermined scenarios, on the basis of the observation data sequence and at least one statistical model stored in memory and associating possible observation data values with the predetermined scenarios;
wherein, the memory storing a plurality of statistical models broken down into a plurality of ordered levels, the selection comprises:
determining intermediate state values on the basis of the observation data sequence and at least one first-level, or input level, statistical model, wherein each statistical model associates possible values of at least a portion of the observation data with intermediate states that are specific to said each statistical model, and
selecting the at least one scenario, on the basis of the intermediate state values and at least one final-level, or output level, statistical model, wherein each statistical model associates possible values of at least a portion of the intermediate states of at least one statistical model from a lower level with at least a portion of the predetermined scenarios;
the method further comprising:
determining a sequence of standardized measurement values of at least a portion of the intermediate states based on at least one statistical model specifically defined to determine that portion of the intermediate states and on values received by said at least one statistical model, wherein measurement values of an intermediate state suitable for being determined by a given statistical model are standardized when the sum of the measurement values of all the intermediate states suitable for being determinable by the given statistical model and at the same time is equal to a predetermined time-independent constant; and
selecting the at least one scenario, on the basis of the sequence of standardized measurement values and at least one output level statistical model,
wherein each statistical model of a level other than the output level has intermediate states from each of which the output is at least part of the sequence of standardized measurement values by imposing that the sum at each time of the intermediate state measurement values of each statistical model of a level other than the output level is equal to a time-independent constant, and the output level determines directly from the outputted sequences of standardized measurement values either one of the scenarios which is selected among the predetermined scenarios or a sequence of scenarios from among the predetermined scenarios.

11. A non-transitory computer-readable medium including computer executable instructions executable by a detection device to execute a method for determining a subject's condition according to claim 10.

* * * * *

UNITED STATES PATENT AND TRADEMARK OFFICE
CERTIFICATE OF CORRECTION

PATENT NO. : 9,235,807 B2
APPLICATION NO. : 13/884814
DATED : January 12, 2016
INVENTOR(S) : Pierre Jallon It is certified that error appears in the above-identified patent and that said Letters Patent is hereby corrected as shown below:

In the Specification

Column 9, line 60, change

" $p(X_N = i | Y_{0:N}) = \frac{1}{p(Y_{0:N})} \alpha_N(i) = \frac{\alpha_N(i)}{\sum_j \alpha_N(i)}$ since the sum of the probabilities equals 1.  (5)"

to -- $\alpha_n(i) = \sum_j \alpha_{n-1}(j) p(Y_n | X_n = i) p(X_n = i | X_{n-1} = j)$  . (4) --.

Column 10, line 2, change

" $\alpha_n(i) = \sum_j \alpha_{n-1}(j) p(Y_n | X_n = i) p(X_n = i | X_{n-1} = j)$  . (4) "

to -- $p(X_N = i | Y_{0:N}) = \frac{1}{p(Y_{0:N})} \alpha_N(i) = \frac{\alpha_N(i)}{\sum_j \alpha_N(i)}$ since the sum of the probabilities equals 1.  (5)--.

Signed and Sealed this
Fifth Day of July, 2016

Michelle K. Lee
*Director of the United States Patent and Trademark Office*